United States Patent
Schnell et al.

(10) Patent No.: US 6,319,465 B1
(45) Date of Patent: Nov. 20, 2001

(54) REVERSING FLOW BLOOD PROCESSING SYSTEM HAVING REDUCED CLOTTING POTENTIAL

(75) Inventors: William J. Schnell, Libertyville, IL (US); David S. Utterberg, Seattle, WA (US); Ting Ting Yu, Grayslake, IL (US)

(73) Assignee: DSU Medical Corporation, Las Vegas, NV (US)

( * ) Notice: Subject to any disclaimer, the term of this patent is extended or adjusted under 35 U.S.C. 154(b) by 0 days.

(21) Appl. No.: 09/325,219

(22) Filed: Jun. 3, 1999

(51) Int. Cl.$^7$ ................................................ A61M 1/14
(52) U.S. Cl. ........................ 422/44; 604/6.1; 604/4.01; 604/6.16; 604/32; 210/646
(58) Field of Search ........................... 604/4.01, 5.01, 604/523, 905, 32, 27, 28, 30, 40, 43, 153; 606/192, 194; 210/644–646, 22, 321.72, 321, 636, 456, 425, 424; 165/158

(56) References Cited

U.S. PATENT DOCUMENTS

| | | | |
|---|---|---|---|
| 4,086,924 | 5/1978 | Latham, Jr. | ............................ 128/214 |
| 4,324,662 | 4/1982 | Schnell . | |
| 4,439,984 | 4/1984 | Martin . | |
| 4,662,871 | 5/1987 | Rafelson . | |
| 4,885,087 | * 12/1989 | Kopf | ................................ 210/321.72 |
| 5,106,363 | 4/1992 | Nobuyoshi | ................................ 604/4 |
| 5,292,308 | 3/1994 | Ryan . | |
| 5,336,165 | 8/1994 | Twardowski . | |

(List continued on next page.)

OTHER PUBLICATIONS

Depner and Krivitski "Clinical Measurement of Blood Flow in Hemodialysis Access Fistula and Grafts by Ultrasound Dilution", ASAIO Journal, Jul.–Sep., 1995, pp. M745–M749.

Mishkin et al. "Specificity and Sensitivity of Ultrasound Dilution for Access Recirculation (AR) Measurements", Journal of the American Society of Nephrology, vol. 7, No. 9, Sep., 1996, one page.

Krivitski "Theory and validation of access flow measurement by dilution technique during hemodialysis", Kidney International, vol. 48, (1995), pp. 244–250.

Kirvitshi, N.M. "Novel Method to Measure Access Flow During Hemodialysis by Ultrasound Dilution Technique" ASAIO Journal, vol. 41, pp. M741–M745, 1995.

Krivistki, N.M. et al. "Accuracy of Dilution Techniques for Access Flow Measurement During Hemodialysis", American Journal of Kidney Diseases, vol. 31, No. 3, pp. 502–508, 1998.

Krivistki, N.M. et al. "Development of a Method for Measuring Hemodialysis Access Flow: From Idea to Robust Technology", Seminars in Dialysis, vol. 11, No. 2, pp. 124–130, 1998.

*Primary Examiner*—Angela D. Sykes
*Assistant Examiner*—Patricia Bianco
(74) *Attorney, Agent, or Firm*—Garrettson Ellis; Seyfarth Shaw

(57) ABSTRACT

A tubular set is provided for use with extracorporeal treatment of blood. The set comprises: a flow reversing valve having a patient arterial line and a patient venous line each separately connected to one side of the valve. A unit arterial line and a unit venous line are each separately connected to the other side of the valve. The patient arterial line connects with the unit arterial line in a first position of a valve, and the patient venous line connects with the unit venous line in the same first valve position. The patient arterial line connects with the patient venous line in a second position of a valve, while the patient venous line connects with the unit arterial line in the same second valve position. The flow reversing valve is movable between the first and second positions by relative rotation of part of the valve and adjacent portions of the respective lines.

35 Claims, 5 Drawing Sheets

U.S. PATENT DOCUMENTS

| | | |
|---|---|---|
| 5,395,348 | 3/1995 | Ryan . |
| 5,453,576 | 9/1995 | Krivitski . |
| 5,454,374 | 10/1995 | Omachi . |
| 5,492,090 | 2/1996 | Bücker . |
| 5,540,668 | 7/1996 | Wilson, Jr. et al. . |
| 5,570,026 | 10/1996 | Buffaloe, IV et al. . |
| 5,595,182 | 1/1997 | Krivitski . |
| 5,605,630 | 2/1997 | Shibata . |
| 5,631,552 | 5/1997 | Ogawa et al. . |
| 5,643,190 | 7/1997 | Utterberg . |
| 5,644,240 | 7/1997 | Brugger . |
| 5,685,989 | 11/1997 | Krivitski et al. . |
| 5,807,258 | 9/1998 | Cimochowski et al. . |
| 5,817,043 | 10/1998 | Utterberg . |
| 5,830,365 | 11/1998 | Schneditz . |
| 5,894,011 | 4/1999 | Prosl et al. . |

* cited by examiner

REVERSING FLOW BLOOD PROCESSING SYSTEM HAVING REDUCED CLOTTING POTENTIAL

BACKGROUND OF THE INVENTION

Hemodialysis and other forms of extracorporeal blood treatment require the removal of blood from a patient by means of an arterial set, passing of the blood to a blood processing device such as a dialyzer, and returning of the blood to the patient again through a venous blood set.

Maintenance of a good blood set access is a major cost of dialysis, which is the most common extracorporeal blood treatment, although other types of blood treatment are also used, for example passing of the blood through an absorption bed for removal of toxins and the like, hemoperfusion, and other forms of blood treatment.

Beyond the initial cost of the surgical procedure to establish a fistula or graft in the patient, the keeping of adequate blood flow in an arterialized vein or synthetic arteriovenous graft of the patient frequently involves secondary surgical intervention for reconstruction of an old blood vessel site on the patient. Alternatively, it may be necessary to establish an entirely new fistula or graft at a new site if the old one fails.

Failure is evidenced typically by stenosis of the blood vessel, or blockage of an implanted catheter or other venous access site, with a consequent reduction in blood flow that eventually shuts down the site. Clotting is also a major cause of reduced blood flow.

If site failure is detected early enough, a less invasive technique such as balloon angioplasty can be employed to open the stenosis at a greatly reduced cost. Early detection of stenosis can be measured by change in pressure in the blood vessel or implant that reflects a restriction beginning to form. The technique described in Omachi U.S. Pat. No. 5,454,374 has been used to measure the baseline pressure access site for early detection of such a pressure change. Another method used by clinicians is to measure recirculation in the vessel during dialysis. As the flow is restricted in the access, the blood pumping rate indicated on the dialysis machine may exceed the flow rate of fresh blood coming into the vessel, so that some is recirculated from the venous access site to the arterial access site in the patient. This leads to inadequate dialysis since already cleansed blood is thus being reprocessed.

Various methods for measuring the degree of recirculation of this type are known. Another method described by Krivitsky determines blood flow in the access as a marker for stenosis. In this method blood set flow and recirculation are compared between arterial and venous flow in the normal orientation, and then with reversed flow between the arterial and venous access sites, which are typically fistula needles which enter the vein. In the prior art, clinicians typically accomplish this by stopping the flow of blood, clamping off all the lines, disconnecting the set or sets from the fistula needles, and then reconnecting the arterial line to the venous fistula while connecting the venous line to the arterial fistula.

Also regarding catheters (which are typically connected to larger veins or even the vena cava) it is known that catheter blockage may be relieved by reversing flow.

By this invention, a flow set is provided for the communication of blood between a patient and a blood processing device in which the flow restriction in a patient access site can be easily monitored without any external disconnection of the connections needed for the normal flow of blood from a patient to a blood processing device such as a dialyzer, and then from the dialyzer back to the patient. Thus, a great improvement in the convenience of use of the tubular set of this invention is provided. Also, breaks in sterility are avoided, since there is no need to make external disconnections in order to test the patency of a patient access site. Also, the tubular set of this invention can be a combined arterial and venous set, while, most often in the prior art, a separate arterial set and a separate venous set are used. This provides convenience of use through the unification of the set.

There is no need to make internal disconnections in order to test the patency of the patient access site blood flow.

Also, the tubular set portion of this invention can be an insertable segment containing a flow reversal valve which can inserted into conventional arterial and venous circuits between the fistula needles and blood tubing. Alternatively, the tubular set portion of this invention can be an integral part of the arterial and venous sets, but connected to a fistula set for connection to the patient at their arterial and venous ends, and generally connected to a dialyzer or other blood processing device. Also, the invention of this application can be used as a combined arterial or venous set, while, most often in the prior art, a separate arterial set with a separate venous set are used.

Catheters which are implanted in the venous system of a patient for dialysis access or the like may develop a "fibrin sheath" on the outside of the catheter within the blood vessel, for example the jugular or subclavian veins or the vena cava. This fibrin sheath coats the outside of the catheter and can extend over the end thereof.

At the outflow port, such a fibrin sheath is generally not too serious a problem since the outflowing blood forces the fibrin sheath open easily. However, at the inflow port of the catheter, the sheath can act as a one-way valve, collapsing with increasing negative pressure to seriously interfere with flow through the catheter.

Upon such an occurrence, by the sets of this invention, the blood flow through such a blood access catheter can be reversed for continuation of a desired medical procedure such as hemodialysis application.

The inventors of this application have previously filed a patent application Ser. No. 09/095,873, filed Jun. 10, 1998, entitled "Reversing Flow Blood Processing System," which application discloses a blood processing system having a reverse flow valve therein so that flow through the arterial and venous fistulas, or other equivalent patient connection equipment, can be reversed without reversing or stopping the blood pump. By the invention of this application, a flow reversal valve is provided in which the blood flow path through the reverse flow valve encounters little stagnant area where blood can pool and thus initiate clotting. The parts of the reversing flow valve of this present application can all be made by molds without the need for side action, resulting in a simpler and less expensive molding process, and thus a less expensive final product of a flow reversing valve. Additionally, the actual position of the reversing flow valve disclosed in this application is intuitively determinable by the user as to whether or not it is in the desired position. Thus, the valve is easy to use, resulting in a tubular set portion which contains a valve having excellent utility for the end user.

DESCRIPTION OF THE INVENTION

The tubular set portion of this invention may be for use with a complete tubular arrangement for the extracorporeal treatment of blood. Alternatively, the tubular set portion may comprise as little as the reversing flow valve itself, or a reversing flow valve and attached flexible arterial and venous conduits for connection with remaining portions of the arterial and venous sets. Also, the tubular set portions may include the entire system, connected to a hemodialyzer, hemofiltration device, or other blood processing device and also in connection with fistulas or other patient access devices.

The tubular set portion of this invention comprises a flow reversing valve; a patient arterial line and a patient venous line, each separately connected to one side of said valve; and a unit arterial line and a unit venous line each separately connected to another side of said valve. The patient arterial line connects through the valve with the unit arterial line in a first position of the valve, and the patient venous line connects with the unit venous line in the same first position. The patient arterial line connects through the valve with the unit venous line in a second position of the valve, while the patient venous line connects with the unit arterial line in the second position. Preferably, all arterial and unit line connections in both valve positions provide straight, laminar blood flow through the valve.

The flow reversal valve is movable between the first and second positions by relative rotation of part of the valve and adjacent portions of the patient's arterial and venous lines with respect to the unit arterial and venous lines. The direction of rotation is preferably parallel to a plane which is perpendicular to the respective patient and unit lines at the valve.

In both positions of the flow reversing valve, blood enters the valve through a line at one side thereof, and exits the valve through a line at the other side. The direction of rotation of the valve to move it between the two positions is transverse to the flow axes of the pair of flow paths passing through the valve. The blood flow is preferably always straight through the flow reversal valve of this invention rather than being forced to curve or angle in its direction of flow through the valve. This provides better, more physiological blood handling compared with a valve where the blood flow is forced around corners in one or both positions of the valve.

Also, the valve of this invention can have an intermediate position, typically between the two flow positions, in which no flow is possible through the valve. This is to be contrasted with Prosl et al. U.S. Pat. No. 5,894,011 relating to a flow reversing device for hemodialysis, in which the flow reversing valve permits flow therethrough in every valve position due to the presence of a channel 14, so that blood continues to flow in a shunting manner even when the valve is not in a preferred flow alignment. To the contrary, by this invention, when the valve is not in one of its two main flow alignments, the flow through the valve is preferably completely shut off.

An advantage of the valve of this invention is that: if the valve is accidentally placed in a configuration other than one of the two main flow configurations during dialysis, flow of blood will be stopped, and not take place through the dialysis circuit. This condition will be immediately signalled by an alarm in the typical dialysis system. To the contrary, in the Prosl et al. situation, where the valve permits flow of blood through it between fluid fittings 8 and 9 in all circumstances, (which fittings lead to the inlet and outlet of the hemodialysis machine), extracorporeal blood will be recirculated over and over without any access back to the patient. Also, the flow of blood through the patient fistula sets to and from the valve will cease, which can accelerate clotting, and no alarm is likely to sound in conventional dialysis machinery. Thus, if the valve-setting mistake is not noticed, clots can form on the patient's side of the valve. Then, when the valve is reopened, those clots will pass through the valve into the extracorporeal system, and also into the patient.

Despite the presence of a flow blocking valve configuration in this invention, the valve can be rotated from the normal to reversed position without having to stop the peristaltic roller pump typical of extracorporeal blood treatment machines. Although blood pressure will increase somewhat, peristaltic pumps are used with resilient flow tubes. Thus pressure does not increase unduly in the one second or so required to switch valve positions and reestablish flow. Further, extracorporeal machine pressure alarms are typically delayed electronically for 3–5 seconds, so this set can switch flow directions without activating conventional alarms.

In one embodiment, the lines which connect to the flow reversing valve each have ends opposed to the flow reversing valve, which ends carry connectors for connection to other flexible tubular portions of the complete tubular arrangement. Alternatively, the flow reversing valve may be an integral part of an entire, integral set for the flow of blood.

It is preferred for the flow reversing valve to carry first and second engaging plates. The first plate has a first pair of ports that respectively engage the patient arterial and the patient venous lines. The second plate has a second pair of ports that respectively engage the unit arterial and unit venous lines. Typically, the plates are positioned generally parallel to each other. The first and second plates are relatively rotatable with respect to each other, and are peripherally sealed, with the effect that either port of the first pair of ports can communicate with either port of the second pair of ports, while being out of communication with the other ports. This variable communication takes place at differing rotatable positions respectively corresponding to the first and second positions of the valve described above.

A stop member may be provided to limit movement of the relatively rotatable plates of the valve to a rotational range between and including the first and second positions.

It is also preferable for a sealing plate to be carried (and typically sealed) to one of the first and second plates. The sealing plate is positioned between the first and second plates, with the sealing plate having a pair of apertures that register with one of the pairs of ports. The sealing plate firmly engages the other of the plates (first or second plates) with a sealed surface. It is preferable that the sealing plate is made of a soft sealing material such as an elastomer.

The sealed surface comprises of plurality of abutting, annular portions of the other plate and the sealing plate which are respectively angled by about 90 degrees to adjacent, abutting, annular portions. This forms a cross sectional zigzag seal area which forms a high performance rotary seal, often capable of maintaining sterile conditions inside of the valve.

It is further preferred for the sealing plate to be made of a resilient material, for example, a thermoplastic elastomer, while the first and second plates are made of substantially rigid material such as polycarbonate, to promote sealing between communicating ports of the first and second plates.

DESCRIPTION OF THE DRAWINGS

Referring to the drawings.

DESCRIPTION OF SPECIFIC EMBODIMENT

Figure 1:
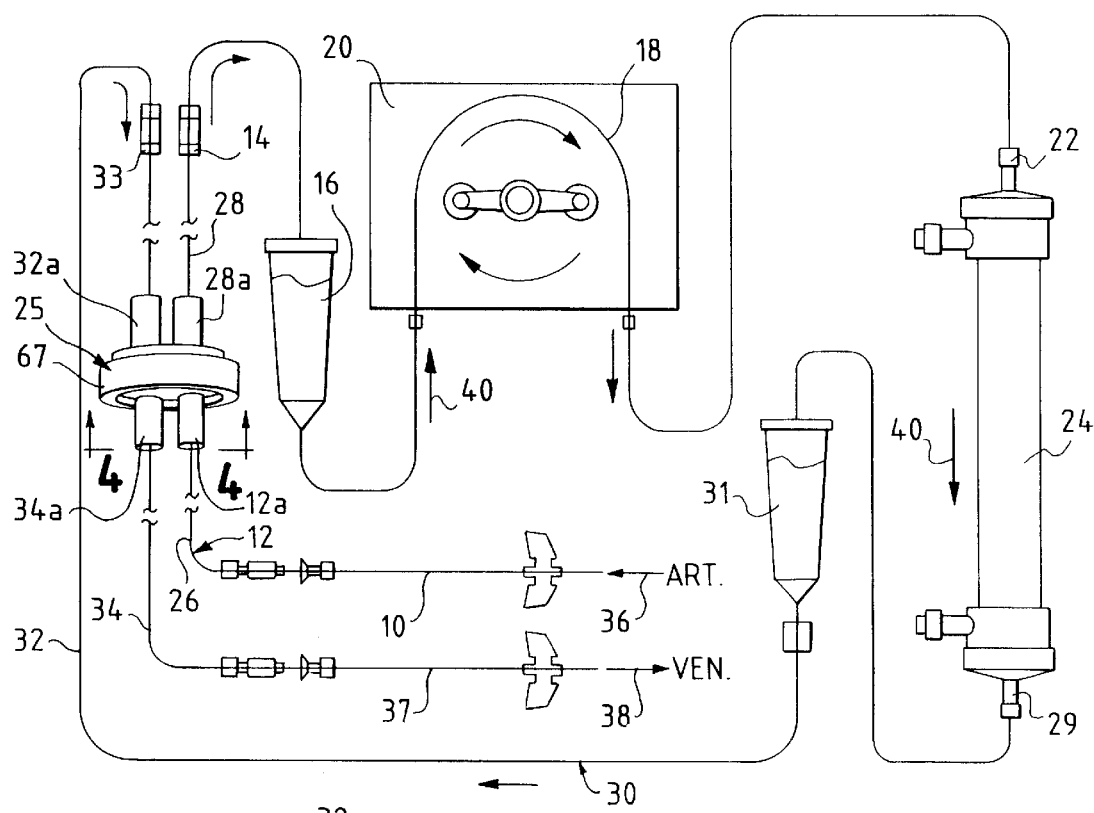
FIG. 1 is a diagrammatic view of a tubular set hemodialysis system in accordance with this invention, showing a first flow pattern.

Referring to the drawings, FIG. 1 shows a tubular arrangement for the extracorporeal treatment of blood. Blood is taken from the vascular system of a patient through arterial fistula set 10, which is conventionally connected to an arterial tube set 12 which carries conventional accessories such as an on-off clamp 14, a bubble removal chamber 16, a length of peristaltic pump tubing 18 which fits within a peristaltic blood pump 20, and a connector 22 which is shown to be connected to the arterial end of a conventional hemodialyzer 24.

Specifically, arterial set 12 comprises a patient arterial line 26 and a unit arterial line 28, both of which are connected to flow valve 25. In the position shown in FIG. 1, blood flows through patient arterial line 26 through valve 25 in a straight-line, laminar flow to patient arterial line 28. From there, the blood flows through bubble chamber 16 and pump tubing 18 to dialyzer 24.

Dialyzed blood passes out of outlet port 29 of dialyzer 24 into venous set 30, which comprises a unit venous line 32 and a patient venous line 34, each of which connects to valve 25, to permit blood to pass from the unit venous line 32 through valve 25 to patient venous line 34 in similar, straight, laminar flow and then to the venous fistula set 37, and from there back to the patient. As is conventional, venous set 30 may contain accessory parts such as bubble removal chamber 31 and on-off flow clamp 33.

The respective arterial set 12 and venous set 30 may each be of entirely conventional design, except as otherwise indicated herein, and may carry the usual branch connection sites, injection sites, and the like for the usual purposes.

As previously described, it may be desirable to reverse the flow of blood in its inlet and outlet from the patient for purposes of obtaining early warning of the formation of an obstruction in a fistula or an implanted vascular access catheter, or for other purposes. Pump 20 remains continuously operating through such reversal, to pump blood through the unit arterial and venous lines 28, 32 without a change in direction and without a significant termination in the flow, particularly a hiatus in the flow that could set off alarms. This can be accomplished by valve 25.

Valve 25 comprises four connection ports that connect with the respective patient arterial and venous lines 12, 34, and the unit arterial and venous lines 28, 32, each port of the valve carrying the number of the line of which it is connected and the suffix a so that there are four connected ports, 12a, 28a, 32a, 34a.

The flow position of valve 25 for normal flow during the hemodialysis process is shown in FIG. 1. Patient arterial line 12, receiving blood from a patient via valve port 12a, passes blood into unit arterial line 28 via valve port 28a as indicated by arrow 36 in FIG. 1. Venous set 30 receives blood from dialyzer 24, passing it through valve 25 to unit venous line 32 by valve port 32a, in a straight, laminar flow to patient venous line 34 via valve port 34a, and from there back to the patient as indicated by arrow 38 of FIG. 1.

Figure 2:
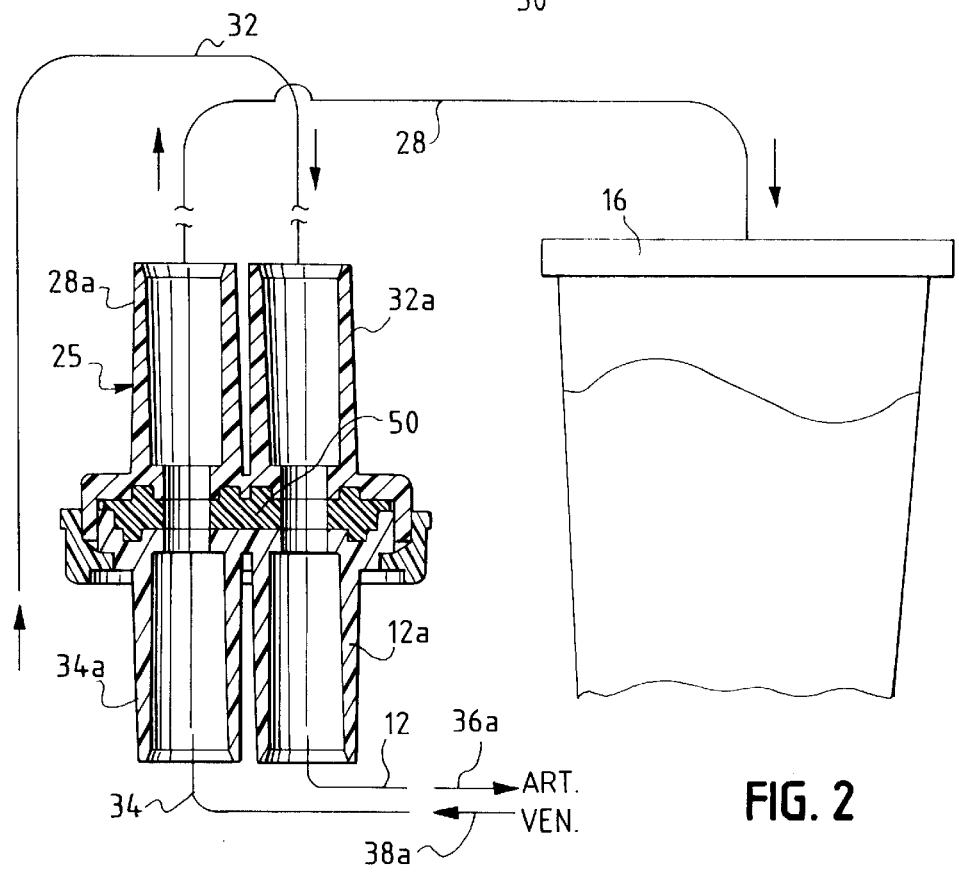
FIG. 2 is a further fragmentary, diagrammatic view showing another flow pattern of the tubular set of FIG. 1 and the flow valve of this invention in a second flow configuration.

When it is desired to reverse the flow relative to the patient, while the flow relative to pump 20 and dialyzer 24 remains unchanged, valve ports 28a and 32a may be horizontally rotated by about 180 degrees relative to valve ports 12a, 34a so that the configuration of valve 25 is changed from that shown in FIG. 1 to the configuration shown in FIG. 2. Alternatively, the actual rotational motion may be performed on valve ports 12a, 34a. It is the relative change of the position of the valve ports that counts.

In the configuration of FIG. 2, the respective ports 12a, 34a of valve 25 communicate with differing ports 28a, 32a from the situation shown in FIG. 1, after a 180 degree rotation of valve ports 28a, 32a. Thus, as pump 20 pumps blood through the tubing of the unit arterial and venous lines in the direction of arrows 40, the direction of blood flow in patient arterial line 12 and patient venous line 34 is reversed, as indicated by arrows 36a, 38a of FIG. 2. Of course, the direction of blood flow through fistula sets 10 and 37 is also reversed.

This change of direction is accomplished very quickly and easily by a simple, 180 degree twist of one pair of respective ports of valve 25, with the flow path thus being changed. The twisting process is so short that pressure alarms will not be set off under normal circumstances in conventional hemodialysis systems.

The flow directions which are normally used for the patient and shown in FIG. 1 can then be reestablished by a simple 180 degree twist of the valve back to its original condition.

Figure 4:
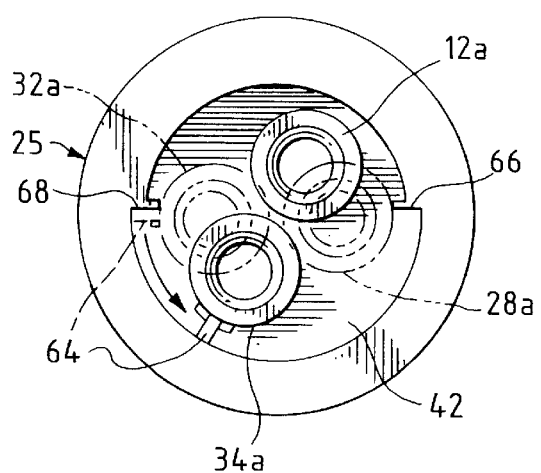
FIG. 4 is a transverse sectional view showing the flow valve in an intermediate position between the first and second operative positions.

If it is desired to shut off flow through valve 25, the pairs of respective ports may be relatively rotated by about 90 degrees, generally a little farther than shown in FIG. 4, to achieve a complete closure of flow through the valve. This facilitates the set up of the system, and may be desirable for use during a brief shut down of dialysis for a variety of reasons. Also, the shut off feature of the valve used in this invention may replace the need for certain external flow clamps on the flexible tubing attached to the reversing flow valve 25.

Figure 3:
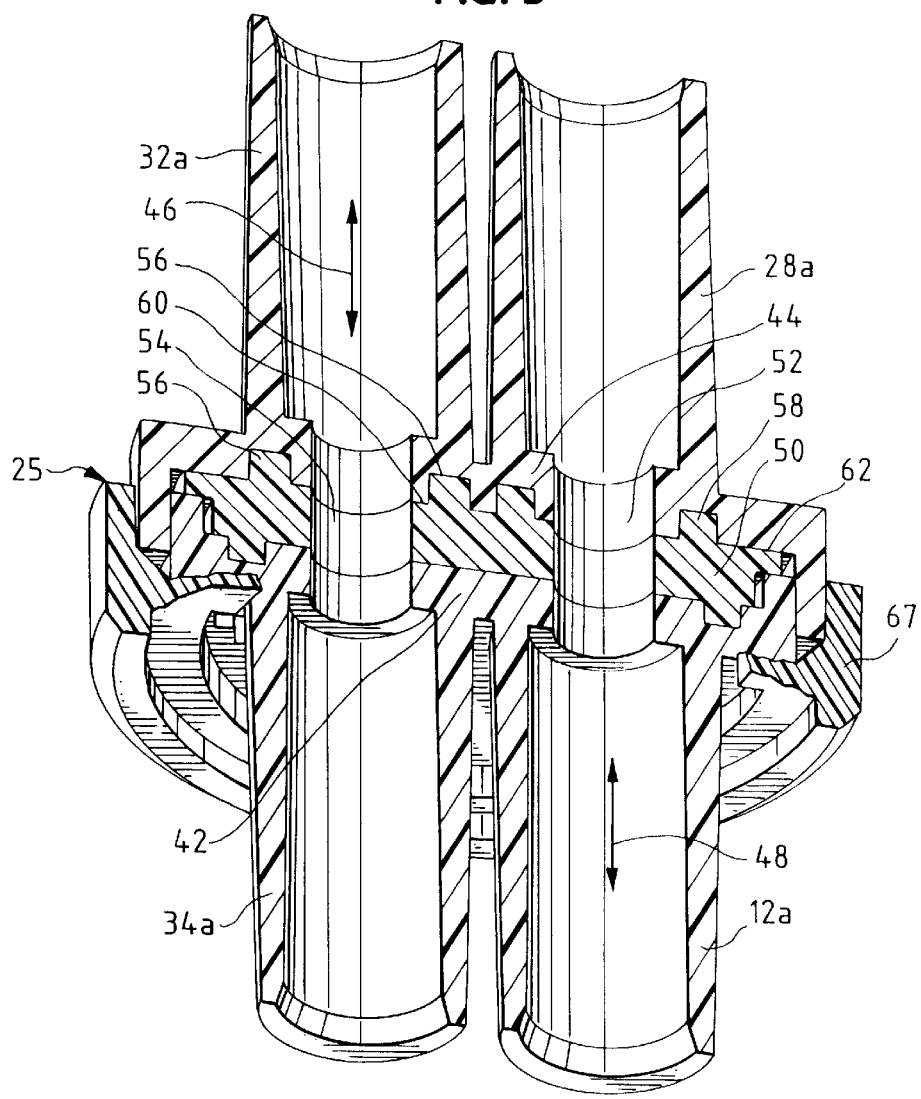
FIG. 3 is a longitudinal sectional perspective view of the flow valve of FIG. 1.

Referring in particular to FIG. 3, patient arterial port 12a and patient venous port 34a, being connected to their corresponding flexible lines 12, 34, are positioned on one side of valve 25 and comprise a single, rotating piece, being carried on first plate 42. Plate 42 also carries housing ring 67. The unit arterial and venous ports 32a, 28a are carried together on a second plate 44, with first plate 42 and second plate 44 being relatively rotatable with respect to each other in a direction parallel to a plane perpendicular to the respective longitudinal axes of ports 12a, 28a, 32a and 34a. These respective axes are exemplified by arrows 46, 48.

Furthermore, valve 25 carries a central sealing plate 50, positioned between first plate 42 and second plate 44. Each of the respective plates defines a separate aperture 52, 54 capable of registering with the other apertures in one of a pair of rotational positions.

Sealing plate 50 may be carried and sealed to one of the first or second plates 42, 44. In this particular embodiment the sealing is to plate 42, so that sealing plate 50 and first plate 42 rotate together as a unit and are sealed to each other by adhesive or the like. Second plate 44 then rotates freely in sealed manner against sealing plate 50 with firm engagement and a sealed surface.

Sealing plate 50 may be made of a resilient material, for example, a thermoplastic elastomer such as Dupont KRATON or the like, or a thermoset elastomer if desired. First and second plates 42, 44 may be made of a substantially rigid material such as a polycarbonate, with the respective ports 12a, 34a being an integral, molded part of first plate 42, and ports 28a, 32a being an integral, molded part of second plate 44. Thus, a highly effective seal is provided by the abutting engagement between the elastomeric sealing plate 50 and the substantially rigid second plate 44.

To further improve the sealing of valve 25, abutting, annular, respective projecting portions and recesses 56, 58 may be defined in sealing plate 50 and second plate 44, such portions being respectively angled by 90 degrees to adjacent abutting, annular portions 60, 62 etc. to form a cross sectional zigzag seal area (the zigzag being seen as a line), which forms a high performance rotary seal around each aperture 52, 54 between sealing plate 50 and second plate 44. The adhesive bond between plates 42 and 50 provides added sealing.

FIG. 4 shows valve 25 in a position with rotation of ports 12a, 34a and the first plate 42, with the process of rotation being incomplete.

Figure 5:
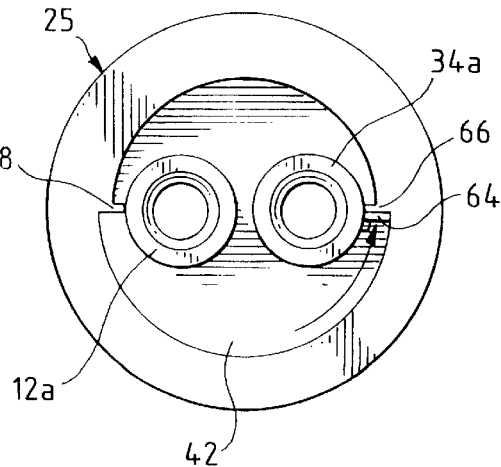
FIG. 5 is a transverse sectional view showing the flow valve of the previous drawings in one of the operative rotary positions.

FIG. 5 shows the complete rotation of valve 25 from the configuration of FIG. 1 to that of FIG. 2, with the available angle of rotation being limited to about 180 degrees by the presence of stop member 64, which is carried on first plate 42, and which engages step member 66 at one extreme of rotation and step member 68 at the other extreme of rotation to limit further rotation.

Figure 7:
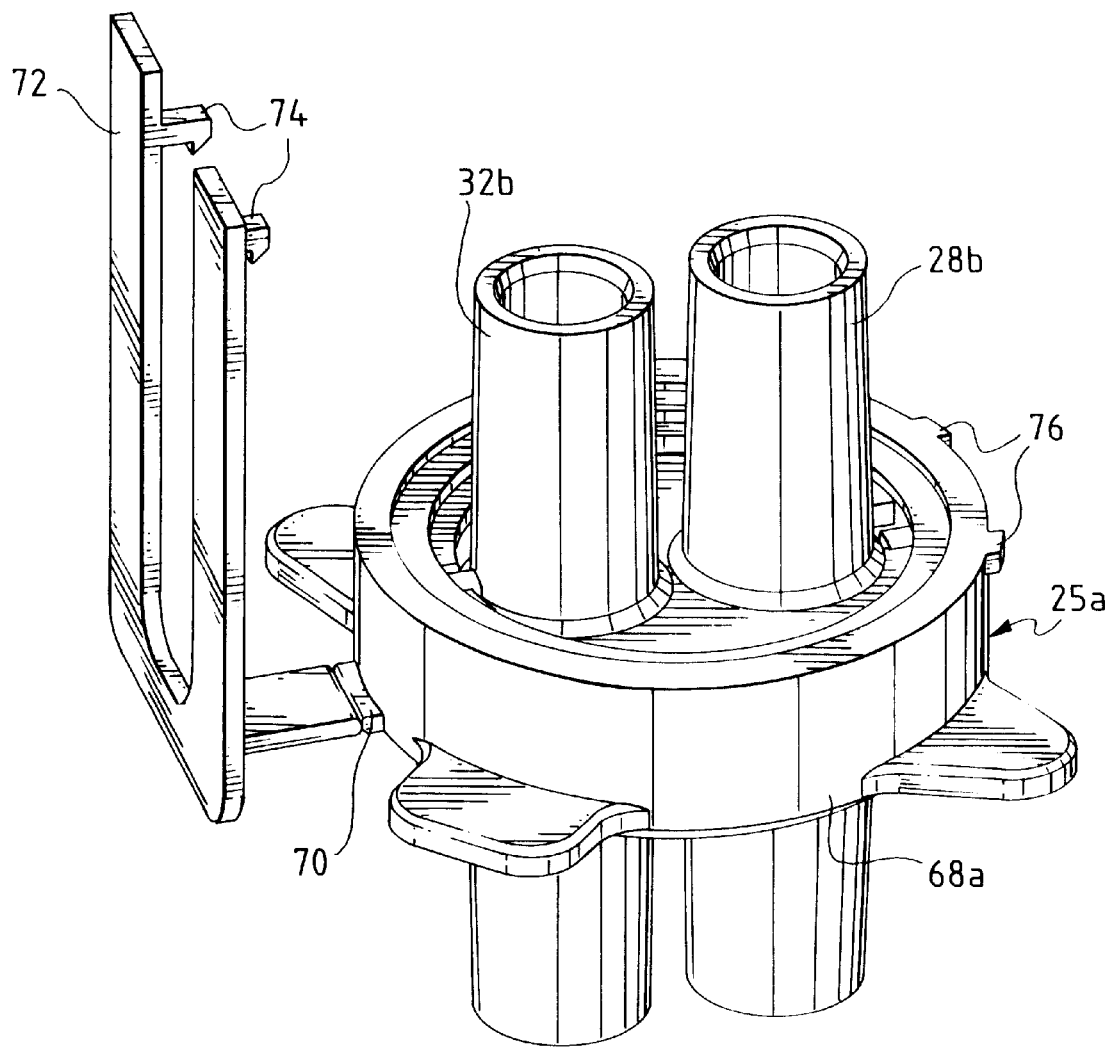
FIG. 7 is a perspective view of another embodiment of reversing flow valve for use in this invention, in which the valve carries a valve lock, shown in the open position.
Figure 8:
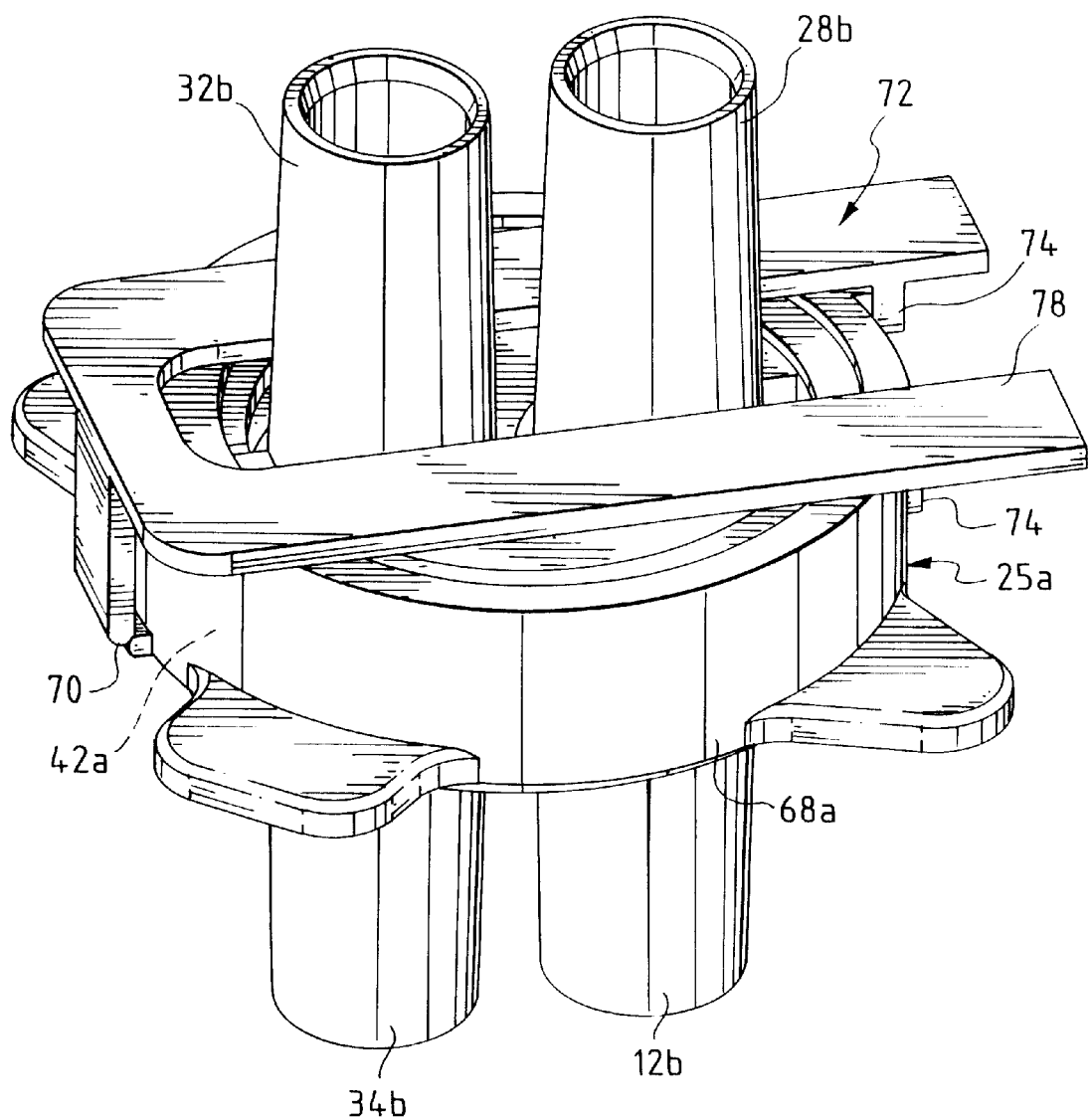
FIG. 8 is a perspective view of the reversing flow valve of FIG. 7 with the valve lock shown in the closed position.

Referring to FIGS. 7 and 8, a reversing flow valve 25a is shown, which is identical in structure and function to reversing flow valve 25, except as otherwise disclosed herein. In particular, the connections of reversing flow valve 25a to various conduits in the extracorporeal blood treatment system shown in particularly in FIG. 1 may be the same as for valve 25.

In accordance with this invention, valve 25 carries a housing ring 68a similar to housing ring 68 as shown in FIG. 3 of the previous embodiment.

Attached to housing ring 68a by an integral, living hinge 70 is a U-shaped retainer member 72, shown in FIG. 7 to be spaced from unit arterial and venous ports 32b, 28b, but capable of being pivoted down to enclose ports 32b, 28b as shown in FIG. 8 in a manner to prevent relative rotation of the four respective ports 12b, 34b, 28b, 32b. Thus, U-shaped retainer 72 can prevent rotation of the respective ports out of either of the two main flow positions, which are 180 degrees apart from each other, since U-shaped retainer 72 is attached to housing ring 68a, which, in turn, is attached to the first plate 42a of valve 25a, similar to first plate 42 as shown in FIG. 3 with respect to valve 25. Patient arterial and venous ports 12b, 34b are carried by first plate 42a.

U-shaped retainer 72 may have snap latches 74 that connect with projections 76 for retention of retainer 72 in the FIG. 8 position. Then, the respective arms of retainer 72 may be spread or the latch disconnected in some other manner to move U-shaped retainer 72 back to the FIG. 7 position, when it is desired to rotate relatively rotate ports 12b, 34b, 28b, 32b to the other main flow position or to the off position.

Thus, reversing flow valve 25a may be locked into either one of its two main flow positions, to avoid accidental movement of the valve out of that desired position.

Thus, a blood flow system is provided for hemodialysis or the like in which a reversing flow valve provides desired reversing flow for testing as previously described or other desired purposes, in which the blood flow through the valve is in all circumstances laminar and straight, for desired better blood handling. The valve also has few or no areas of stagnancy to promote blood clotting, and the valve is easily operated for a rapid change of position without any need to shut off blood pump 20 or other blood flow drives. The valve parts used in this invention also are manufacturable with relatively low cost molds which have no need for side action, and thus are cheaper molds.

Figure 6:
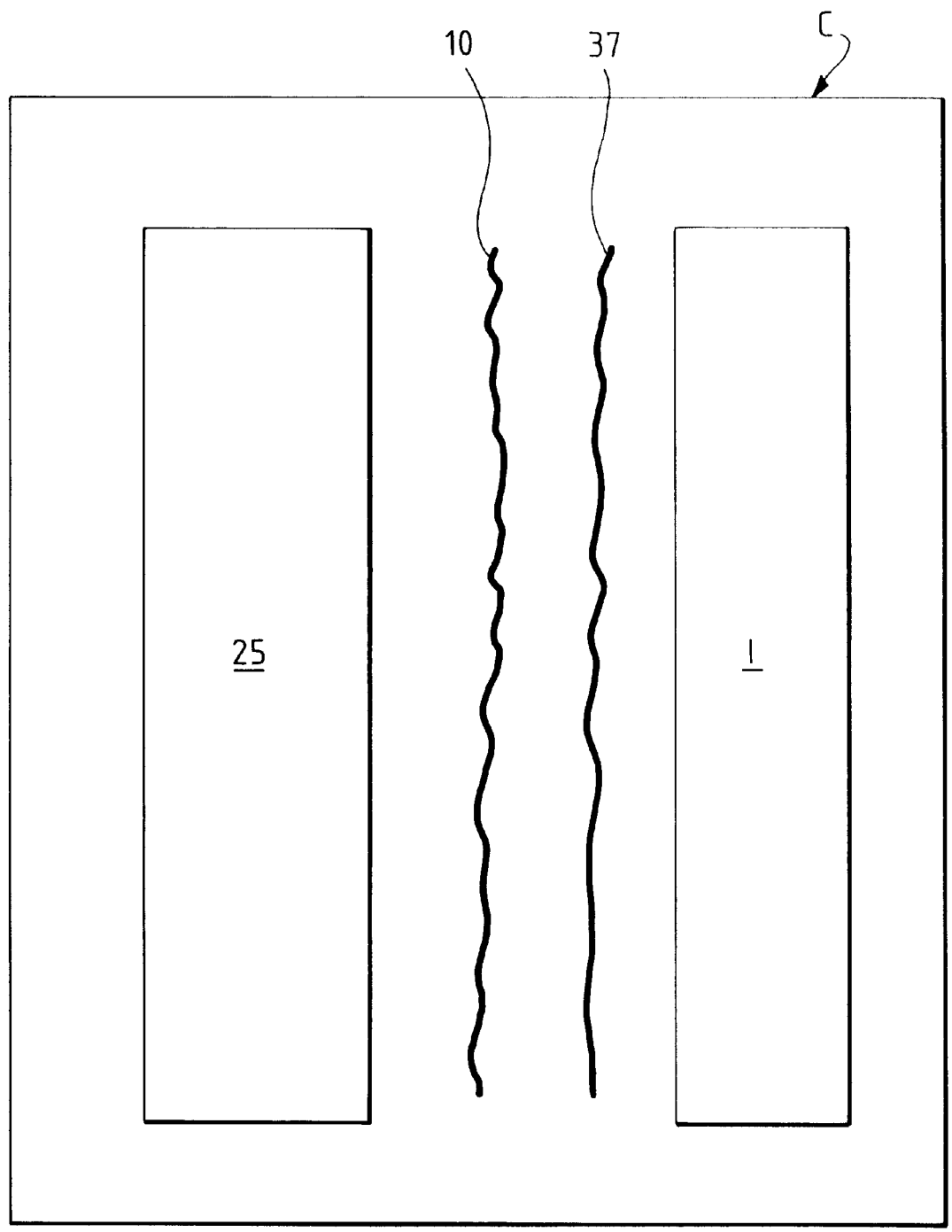
FIG. 6 is a schematic view of a package for the flow valve-containing tubular set of this invention.

Referring to FIG. 6, a conventional container or package C is provided for packaging the hemodialysis set which may comprise flow valve 25 and all or part of the respective arterial set 12 and venous set 30 for connection to a dialyzer or, if desired, packaged in connection with dialyzer. Also, optionally, the fistula sets 10, 37 may be included along with instructions I for use of the arterial and venous sets in conjunction with valve 25 for achieving the desired advantages that result from the reversed flow capability on the patient side of valve 25 provided by this invention. Container or package C may be a conventional tray, pouch or the like.

The above has been offered for illustrative purposes only, and is not intended to the limit the scope of the invention of this application, which is as defined in the claims below.

That which is claimed:

1. A tubular set portion for use with a complete tubular arrangement for the extracorporeal treatment of blood, which set portion comprises:

a flow reversing valve;

a patient arterial line and a patient venous line, each separately connected to one side of said valve;

a unit arterial line and a unit venous line, each separately connected to another side of said valve;

said patient arterial line connected with the unit arterial line in a first position of said valve and said patient venous line connected with the unit venous line in said first position of said valve;

said patient arterial line connected with the unit venous line in a second position of said valve, and said patient venous line connected with the unit arterial line in said second position of the valve;

said flow reversing valve being movable between said first and second positions by relative rotation of part of valve and adjacent portions of the patient arterial and venous lines with respect to the unit arterial and venous lines; said flow reversing valve defining a third position in which no flow is possible between the respective patient and the unit arterial and venous lines.

2. The tubular set portion of claim 1 in which said lines each have ends opposed to said flow reversing valve that carry connectors for connection to other tubular portions of said complete tubular arrangement.

3. The tubular set portion of claim 1 in which said flow reversing valve carries first and second engaging plates, said first plate having a first pair of ports that respectively engage the patient arterial and venous lines, the second plate having a second pair of ports that respectively engage the unit arterial and venous lines, said first and second plates being relatively rotatable and peripherally sealed, whereby either port of said first pair can communicate with either port of the second pair at differing rotatable positions respectively corresponding to said first and second positions.

4. The tubular set portion of claim 3 in which a stop member limits movement of said relatively rotatable plates to a rotational range between and including said first and second positions.

5. The tubular set portion of claim 3 in which a sealing plate is carried by one of said first and second plates and positioned between said first and second plates, said sealing plate having a pair of apertures that register with one of said pairs of ports, said sealing plate firmly engaging the other of said plates with a seal surface.

6. The tubular set portion of claim 5 in which said seal surface of the valve comprises a plurality of abutting, annular, peripheral portions of said other plate and said sealing plate which are respectively angled about 90° to adjacent, abutting, annular, peripheral portions, to form a high performance rotary seal.

7. The tubular set portion of claim 6 in which said sealing plate is made of a resilient material, while said first and second plates are made of substantially rigid materials, to promote sealing between communicating ports of said first and second plates.

8. The tubular set portion of claim 7 in which a stop member limits movement of said relatively rotatable plates to a rotational range between and including said first and second positions.

9. The tubular set portion of claim 5 in which said sealing plate is made of a resilient material, while said first and second plates are made of substantially rigid materials, to promote sealing between communicating ports of said first and second plates.

10. The tubular set portion of claim 1 in which a locking member is provided to retain said valve either in said first position or said second position.

11. The tubular set portion of claim 10 in which said locking member comprises a U-shaped member carried in hinged relation with said flow reversing valve and pivotable to retain one pair of said patient arterial and venous lines or said unit arterial and venous lines, to prevent relative rotation of the respective lines.

12. The tubular set portion of claim 1 in which said flow reversing valve defines a zone of a plurality of said third positions between said first and second positions in which no flow is possible in said zone of third positions between the respective patient and unit arterial and venous lines.

13. A tubular set for the extracorporeal treatment of blood, which set comprises flexible tubing plus the set portion and flow reversing valve of claim 1.

14. A tubular set for the extracorporeal treatment of blood, which set comprises flexible tubing plus the set portion and flow reversing valve of claim 1.

15. A tubular set portion for use with a complete tubular arrangement for the extracorporeal treatment of blood, which set portion comprises:

A flow reversing valve;

A patient arterial line and a patient venous line, each separately connected to one side of said valve;

A unit arterial line and a unit venous line, each separately connected to another side of said valve;

Said patient arterial line connected with the unit arterial line in a first position of said valve and said patient venous line connected with the unit venous line in said first position of said valve.

Said patient arterial line connected with the unit venous line in a second position of said valve; and said patient venous line connected with the unit arterial line in said second position of the valve;

Said flow reversing valve being moveable between said first and second positions by relative rotation of part of the valve and adjacent portions of the patient arterial and venous lines with respect to the unit arterial and venous lines, said flow reversing valve carrying first and second engaging plates, said first plate having a first pair of ports that respectively connect to the patient arterial and venous lines, the second plate having a second pair of ports that respectively connect to the unit arterial and venous lines, said first and second plates being relatively rotatable and sealed at a surface, whereby either port of said first pair can communicate with either port of the second pair at differing rotatable positions respectively corresponding to said first and second positions; and a stop member carried on each of said plates peripherally outside of said unit and patient arterial and venous lines to limit movement of said plates to a rotational range between and including said first and second positions;

said lines each having ends opposed to said flow reversing valve that carry connectors for connection to other portions of said complete tubular arrangements.

16. The tubular set portion of claim 15 in which a sealing plate is carried by one of said first and second plates and positioned between said first and second plates, said sealing plate having a pair of apertures that register with one of said pairs of ports, said sealing plate firmly engaging the other of said plates with a seal surface.

17. The tubular set portion of claim 16 in which said flow reversing valve defines a third position in which no flow is possible between the respective patient and unit arterial and venous lines.

18. The tubular set portion of claim 17 in which said seal surface of the valve comprises a plurality of abutting, annular, peripheral portions of said other plate and said sealing plate which are respectively angled about 90 degrees to adjacent, abutting, annular, peripheral portions, to form a high performance rotary seal.

19. The tubular set portion of claim 18 in which said sealing plate is made of a resilient material, while said first and second plates are made of substantially rigid materials, to promote sealing between communicating ports of said first and second plates.

20. The tubular set portion of claim 15 in which a sealing plate is carried by one of said first and second plates and positioned between said first and second plates, said sealing plate having a pair of apertures that register with one of said pairs of ports, said sealing plate firmly engaging the other of said plates with a seal surface.

21. The tubular set portion of claim 20 in which said sealing plate is made of a resilient material, while said first and second plates are made of substantially rigid materials, to promote sealing between communicating ports of said first and second plates.

22. The tubular set portion of claim 21 in which a locking member is provided to retain said valve either in said first position or said second position.

23. The tubular set portion of claim 22 in which said locking member comprises a U-shaped member carried in hinged relation with said flow reversing valve and pivotable to retain one pair of said patient arterial and venous lines or said unit arterial and venous lines to prevent relative rotation of the respective lines.

24. The method of performing an extracorporeal treatment of blood, which comprises the steps of: (1) drawing blood from a patient through a patient arterial line and passing said blood from the patient arterial line to a unit arterial line through a moveable valve with straight, laminar flow; passing blood from the unit arterial line to a blood processing unit; passing blood from the blood processing unit to a unit venous line; passing blood from the unit venous line to a patient venous line through said moveable valve with straight, laminar flow, and from there back to the patient, said process further including the step of (2) switching the connections of said line without external disconnection and reconnection, said switching being accomplished by moving said valve between first and second flow-permitting positions in which, during said switching of the connection of said lines, said valve is moved through a flow-blocking zone to block flow through said valve; and, thereafter, (3) passing blood from the patient through the patient venous line and then through said valve with straight, laminar flow to the unit arterial line; passing blood from the unit arterial line through the connected blood processing unit to the unit venous line; passing blood from the unit venous line through the valve with straight, laminar flow to the patient arterial line, and returning blood from the patient arterial line to the patient.

25. The method of claim 24 in which said movable valve is moved while continuing flow of blood through said patient and unit lines.

26. A tubular set portion for use with a complete tubular arrangement for the extracorporeal treatment of blood, which set portion comprises:

a flow reversing valve;

a patient arterial line and a patient venous line, each separately connected to one side of said valve;

a unit arterial line and unit venous line, each separately connected to another side of said valve;

said patient arterial line connected with the unit arterial line in the first position of said valve and said patient venous line connected with the unit venous line in said first position of said valve;

said patient arterial line connected with the unit venous line in a second position of said valve and said patient venous line connected with the unit arterial line in said second position of the valve;

said flow reversing valve being movable between said first and second positions by relative rotation of part of the valve and adjacent portions of the patient arterial and venous lines with respect to the unit arterial and venous lines; in which said flow reversing valve carries first and second engaging plates, said first plate having a first pair of ports that respectively engage the patient arterial and venous lines, the second plate having a second pair of ports that respectively engage the unit arterial and venous lines, said first and second plates being relatively rotatable and peripherally sealed, whereby either port of said first pair can communicate with either port of the second pair at differing rotatable positions respectively corresponding to said first and second positions, and further in which a sealing plate is positioned between said first and second plates, and connected to one of said first and second plates, said sealing plate having a pair of apertures that register with one of said pairs of ports, said sealing plate firmly engaging the other of said plates with a seal surface.

27. The tubular set portion of claim 26 in which said sealed surface of the valve comprises a plurality of abutting, annular, peripheral portions of said other plate and said sealing plate which are respectively angled about 90 degrees to adjacent, abutting, annular peripheral portions, to form a high performance rotary seal.

28. The tubular set portion of claim 27 in which said sealing plate is made of a resilient material, while said first and second plates are made of substantially rigid materials, to promote sealing between communicating ports of said first and second plates.

29. The tubular set portion of claim 28 in which a stop member, positioned adjacent the periphery of said valve, limits movement of said relatively rotatable plates to a rotatable range between and including said first and second positions.

30. The tubular set portion of claim 26 in which a locking member is provided to retain said valve either in said first position or said second position.

31. The tubular set portion of claim 30 in which said locking member comprises a U-shaped member carried in hinged relation with said flow reversing valve and pivotable to retain one pair of said patient arterial and venous lines or said unit arterial and venous lines, to prevent relative rotation of the respective lines.

32. The tubular set portion of claim 26 in which the flow reversing valve defines a zone between said first and second positions in which no flow is possible between the respective patient and unit arterial and venous lines.

33. A tubular set for the extracorporeal treatment of blood, which set comprises flexible tubing plus the set portion and flow reversing valve of claim 26.

34. A tubular set portion for use with a complete tubular arrangement for the extracorporeal treatment of blood, which set portion comprises:

a flow reversing valve;

a patient arterial line and a patient venous line, each separately connected to one side of said valve;

a unit arterial line and a unit venous line, each separately connected to another side of said valves;

said patient arterial line connected with the unit arterial line in a first position of said valve and the patient venous line connected with the unit venous line in said first position of said valve;

said patient arterial line connected with the unit venous line in a second position of said valve and said patient venous line connected with the unit arterial line in said second position of the valve;

said flow reversing valve being movable between said first and second positions by relative rotation of part of the valve and adjacent portions of the patient arterial and venous lines with respect to the unit arterial and venous lines; further in which a locking member is provided to retain said valve either in said first position or said second position.

35. A tubular set portion of claim 34 in which said locking member comprises a U-shaped member carried in hinged relation with said flow reversing valve and pivotable to retain one pair of said patient arterial and venous lines or said unit arterial and venous lines, to prevent relative rotation of the respective lines.

* * * * *